(12) United States Patent
Lu et al.

(10) Patent No.: US 9,499,798 B2
(45) Date of Patent: Nov. 22, 2016

(54) METHOD FOR INDUCING FUSION OF DENDRITIC CELL WITH TUMOUR CELL

(71) Applicant: Yongxiang Zhao, Nanning, Guangxi (CN)

(72) Inventors: Xiaoling Lu, Nanning (CN); Yi Peng, Nanning (CN)

(73) Assignee: Yongxiang Zhao, Nanning (CN)

( * ) Notice: Subject to any disclaimer, the term of this patent is extended or adjusted under 35 U.S.C. 154(b) by 26 days.

(21) Appl. No.: 14/426,163

(22) PCT Filed: Mar. 7, 2013

(86) PCT No.: PCT/CN2013/072295
§ 371 (c)(1),
(2) Date: Mar. 5, 2015

(87) PCT Pub. No.: WO2014/040405
PCT Pub. Date: Mar. 20, 2014

(65) Prior Publication Data
US 2015/0252331 A1 Sep. 10, 2015

(30) Foreign Application Priority Data

Sep. 11, 2012 (CN) .......................... 2012 1 0333205

(51) Int. Cl.
*C12N 5/16* (2006.01)
*A61K 39/00* (2006.01)

(52) U.S. Cl.
CPC ............. *C12N 5/16* (2013.01); *A61K 39/0011* (2013.01); *A61K 2039/5152* (2013.01); *A61K 2039/5154* (2013.01); *C12N 2500/50* (2013.01); *C12N 2502/1121* (2013.01); *C12N 2502/30* (2013.01)

(58) Field of Classification Search
CPC . C12N 5/16; C12N 2502/30; C12N 2500/50
USPC ....................................................... 435/346
See application file for complete search history.

(56) References Cited

U.S. PATENT DOCUMENTS

2006/0018880 A1* 1/2006 Ratliff .................. A61K 38/191
424/93.2

OTHER PUBLICATIONS

Lee et al. (Cell Fusion in Health and Disease. 2001, pp. 177-186).*
Bunyaratavej et al. (J Periodontol, Feb. 2001, 72: 215-229).*

* cited by examiner

*Primary Examiner* — Yan Xiao

(57) ABSTRACT

Disclosed in the present invention is a method for inducing the fusion of a dendritic cell with a tumour cell, in the fusion process, successively adding an amount of polyethylene glycol and collagen to induce cell fusion highly efficiently, wherein polyethylene glycol can make the lipid molecules of the plasma membrane at the contact point between the two cells disperse and recombine, and then the cells fuse due to the mutual affinity between the bilayer membranes at the interface of the two cells and the surface tension between each other. The collagen can retrench the cell membrane and repair the cell membrane after fusion, thereby forming stable fusion cells highly efficiently, so it is suitable for the production of specific biological products such as tumour vaccines and monoclonal antibodies etc.

6 Claims, 4 Drawing Sheets

METHOD FOR INDUCING FUSION OF DENDRITIC CELL WITH TUMOUR CELL

FIELD OF THE APPLICATION

The present application relates to the field of medical biotechnology, and more particularly to a method for inducing fusion of dendritic cell with tumour cell.

BACKGROUND OF THE APPLICATION

Dendritic cells (DC) have the most efficient antigen-presenting function among antigen-presenting cells (collagen PC) in the body. The dendritic cells not only can express richly MHC-I molecules, MHC-II molecules, costimulatory molecules, adhesion molecules and high level Th1 type response predominant factor IL-12 respectively, but also can effectively activate homologous lymphocytes to generate antigen specific immune responses, which has become the focus in the field of tumour biotherapy recently. One key problem is how to enable the DCs to effectively present the tumour antigens. In recent years, people have tried to use different tumour antigens such as polypeptides, tumour cell lysates, tumour cell apoptosis products, etc, or to use gene engineering to transfer tumour antigen genes into the DCs by carriers. Sensitized DC vaccines can induce to form CTL cells in vivo and vitro and stimulate effective specific anti-tumour immune function within human body. Also, the sensitized DC vaccines have been proved to be effective for therapeutic trial of malignant tumour. However, in view of the fact that few antigens have been known so far, most of the tumour antigens are unknown. Thus scientists directly fuse the DCs with tumour cells, so that the DCs are ensured to express and present a variety of antigens on the basis of obtaining all the genes of the tumour cells, as well as to induce polyclonal immune response resisting to a wide variety of tumour antigens (including known and unknown one(s)), which has shown an exciting curative effect on tumour.

When the DCs directly fuse with the tumour cells, relatively low fusion efficiency has always been a difficult issue during research, and thus how to improve the fusion efficiency needs to be solved urgently. At present, three kinds of existing research methods can be used for inducing cell fusion: biological method (e.g., virus induced fusion method), chemical method (e.g., polyethylene glycol (PEG) induced fusion method), and physical method (e.g., electric field induced fusion method). There are a number of problems when using inactivated viruses to induce cell fusion, such as difficult preparation for viruses, complex operation, large difference of inactivated virus titer, poor reproducibility of experiments, and low fusion rate, etc. Because virus induced cell fusion has too many disadvantages, PEG induced cell fusion has gradually developed into a normative and important chemical fusion method since 1975. The advantage of the PEG method is that there is no specificity or selectivity between species, between genera or between families, so the PEG method has been still in use today. The PEG method has been widely used in many experiments with its low experimental cost and high fusion rate. Though there are lots of successful reports about PEG used as a fusion agent, there are still defects of low fusion rate and large empirical property.

SUMMARY OF THE APPLICATION

The object of the present application is to provide a method for inducing fusion of dendritic cell with tumour cell aiming at the existing defects of low fusion rate.

The technical solution of the present application to solve the technical problems mentioned above is to establish a method for inducing fusion of dendritic cell with tumour cell. The method comprises the following steps:

Step 1, collecting tumour cells in a centrifuge tube A, collecting dendritic cells in a centrifuge tube B, respectively centrifuging the centrifuge tube A and the centrifuge tube B for 10 minutes at 1500 rpm at room temperature, re-suspending the cells in the centrifuge tube A and the centrifuge tube B respectively with phosphate buffer and counting the cells thereafter;

Step 2, adding the tumour cells in the centrifuge tube A and the dendritic cells in the centrifuge tube B into a centrifuge tube C according to a quantity proportion of the tumour cells to the dendritic cells of 1 to 2-5 while controlling a total number of the cells to range from $1 \times 10^7$ to $5 \times 10^7$, mixing the cells by whirling, centrifuging the centrifuge tube C for 10 minutes at 1500 rpm at room temperature, removing supernatant and placing the centrifuge tube C in a water bath of 40° C. for 3-5 minutes;

Step 3, placing polyethylene glycol with a molecular weight from 1500 to 6000 into the water bath of 40° C. for 2 minutes, adding 200 μl-1000 μl polyethylene glycol into the centrifuge tube C within one minute, mixing the cells, and placing the centrifuge tube C in the water bath of 40° C. for 3-5 minutes;

Step 4, first adding 1 ml phosphate buffer into the centrifuge tube C within one minute to stop reacting, then adding and mixing 30 ml-40 ml phosphate buffer in the centrifuge tube C within 3-5 minutes; centrifuging the centrifuge tube C for 10 minutes at 1500 rpm at room temperature, removing the supernatant, adding and mixing 30 ml-40 ml phosphate buffer in the centrifuge tube C; centrifuging the centrifuge tube C for 10 minutes at 1500 rpm at room temperature, removing the supernatant, and adding 200 μl-800 μl phosphate buffer into the centrifuge tube C to re-suspend the cells;

Step 5, adding 2 μl-8 μl collagen into the centrifuge tube C, and placing the centrifuge tube C in a water bath of 37° C. for 30-50 minutes;

Step 6, adding and mixing 30 ml phosphate buffer in the centrifuge tube C, centrifuging the centrifuge tube C for 10 minutes at 1500 rpm at room temperature, removing the supernatant, adding 1640 complete culture medium into the centrifuge tube C and re-suspending the cells to obtain fusion cells. In the method for inducing fusion of dendritic cell with tumour cell of the present application, the collagen of the step 5 has a relative molecular weight ranging from 1600 to 4000 and a mass-to-volume ratio of 50%.

In the method for inducing fusion of dendritic cell with tumour cell of the present application, the collagen of the step 5 is collagen I.

In the method for inducing fusion of dendritic cell with tumour cell of the present application, the polyethylene glycol of the step 3 has a relative molecular weight ranging from 1600 to 4000 and a mass-to-volume ratio of 50%.

In the method for inducing fusion of dendritic cell with tumour cell of the present application, 300 μl-1000 μl polyethylene glycol is adopted in the step 3.

By implementing the method for inducing fusion of dendritic cell with tumour cell of the present application, the following advantages can be achieved: the polyethylene glycol adopted by the fusion method of the present application can make the lipid molecules of the plasma membrane at the contact point between the two cells disperse and recombine, and then the cells fuse due to the mutual affinity between the bilayer membranes at the interface of the two cells and the surface tension between each other; the collagen can retrench the cell membrane and repair the cell membrane after fusion, thereby forming stable fusion cells; the method of the present application is proved to be high in fusion efficiency and low in cell damage by detections of fluorescence microscope and confocal microscope and cell experiments.

DETAILED DESCRIPTION OF THE PREFERRED EMBODIMENT

In order to understand the object, the technical features and the advantages of the present application more clearly, the present application will be further described in detail with reference to specific embodiments and drawings.

The present application provides a method for efficiently inducing fusion of dendritic cell with tumour cell by using polyethylene glycol (PEG) and collagen together. The method is simple, easy to obtain, excellent in repeatability, high in cell fusion efficiency and low in cell damage, so it is suitable for the production of specific biological products such as tumour vaccines and monoclonal antibodies etc. This fusion method has important significance in the aspects of cell differentiation research, gene mapping research, and tumourigenesis mechanism research and so on. In practical application, this fusion technique plays an important role in the aspects of targeted drug release system, cell therapy, and anti-tumour immunity and so on.

Figure 1:
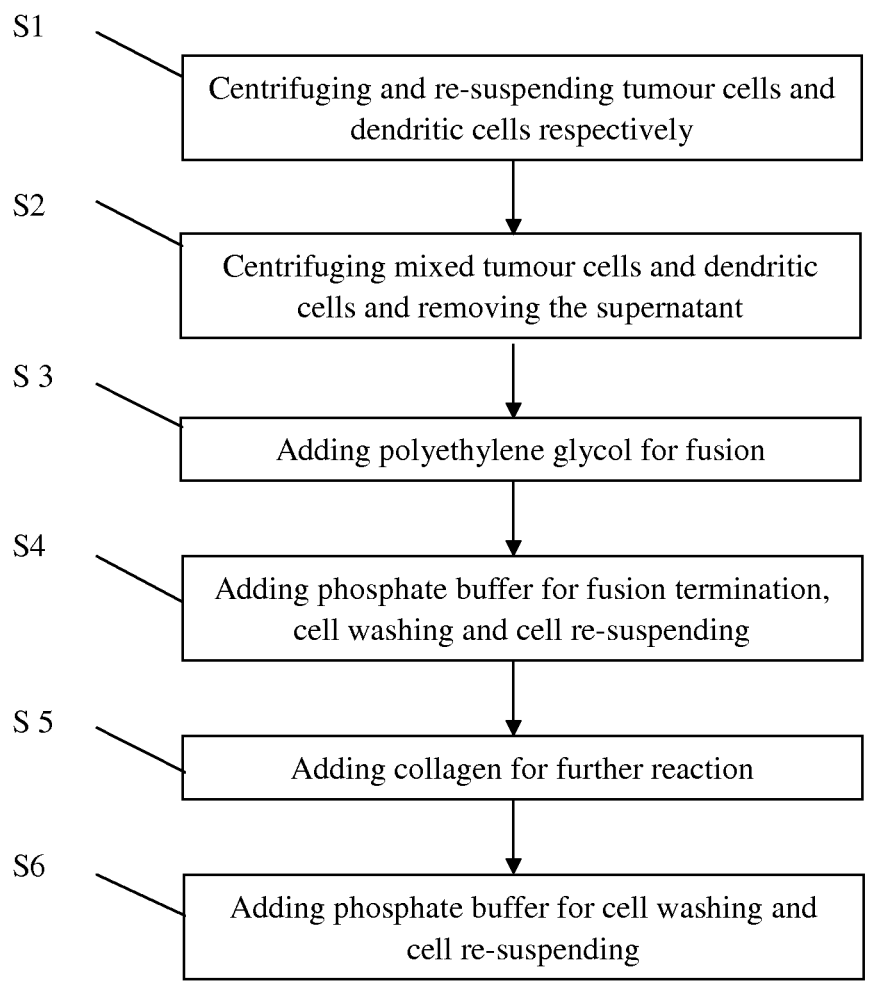
FIG. 1 is a flow diagram of a method for inducing fusion of dendritic cells with tumour cells provided by the present application.

FIG. 1 is a flow diagram of the method for inducing fusion of dendritic cell with tumour cell provided by the present application. Referring to FIG. 1, the method comprises steps as follow.

First, in step 1, tumour cells and dendritic cells are centrifuged and re-suspended respectively. Specifically, phosphate buffer, collagen and 1640 complete culture medium are in advance placed into a water bath of 37° C. respectively for latter usage.

The tumour cells are digested and collected in a centrifuge tube A, and the suspending dendritic cells are collected in a centrifuge tube B. The centrifuge tube A and the centrifuge tube B are respectively centrifuged for 10 minutes at 1500 rpm at room temperature. The cells in the centrifuge tube A and the centrifuge tube B are respectively counted after being re-suspended with the phosphate buffer.

Subsequently, in step 2, the tumour cells and the dendritic cells are mixed and centrifuged to remove the supernatant. Specifically, two types of cells respectively in the centrifuge tube A and in the centrifuge tube B are both added into a centrifuge tube C according to a quantity proportion of the tumour cells to the dendritic cells of 1 to 2-5 and mixed by whirling, where the total number of the cells are controlled to range from $1\times10^7$ to $5\times10^7$. Then the centrifuge tube C is centrifuged for 10 minutes at 1500 rpm at room temperature to remove the supernatant, and the centrifuge tube C is flicked with fingers to achieve relatively uniform cell distribution. After that, the centrifuge tube C is placed into a water bath of 40° C. for 3-5 minutes. The centrifuge tubes A, B and C may have a volume of 50 ml.

Subsequently, in step 2, the tumour cells and the dendritic cells are mixed and centrifuged to remove the supernatant. Specifically, two types of cells respectively in the centrifuge tube A and in the centrifuge tube B are both added into a centrifuge tube C according to a quantity proportion of the tumour cells to the dendritic cells of 1 to 2-5 and mixed by whirling, where the total number of the cells are controlled to range from $1\times10^7$ to $5\times10^7$. Then the centrifuge tube C is centrifuged for 10 minutes at 1500 rpm at room temperature to remove the supernatant, and the centrifuge tube C is flicked with fingers to achieve relatively uniform cell distribution. After that, the centrifuge tube C is placed into a water bath of 40° C. for 3-5 minutes. The centrifuge tubes A, B and C may have a volume of 50 ml.

Subsequently, in step 4, the phosphate buffer is added for fusion termination, cell washing and cell re-suspending. Specifically, the phosphate buffer of 1 ml is first added into the centrifuge tube C for reaction termination, which is required to be finished within one minute. Then the phosphate buffer of 30 ml-40 ml is slowly added into the centrifuge tube C, where this operation is required to be finished within 3-5 minutes, and the phosphate buffer is being added with rotating the centrifuge tube C. After adding, a cover of the centrifuge tube is covered, and the centrifuge tube C is rotated to mix the solution to achieve full reaction termination. Afterwards the centrifuge tube C is centrifuged for 10 minutes at 1500 rpm at room temperature, the supernatant is removed, and the phosphate buffer of 30 ml-40 ml is slowly added into and mixed within the centrifuge tube C (for example, finishing the adding operation within 3-5 minutes and rotating the centrifuge tube C during adding process). After adding, the cover of the centrifuge tube is covered, and the centrifuge tube is rotated to achieve full washing. Then the centrifuge tube C is again centrifuged for 10 minutes at 1500 rpm at room temperature, the supernatant is removed, and the phosphate buffer of 200 μl-800 μl is added into the centrifuge tube C to re-suspend the cells.

Subsequently, in step 5, the collagen is added for further reaction. Specifically, the collagen of 2 μl-8 μl is added into the centrifuge tube C. Preferably, 3 μl-5 μl collagen is added here. The centrifuge tube C is then heated in the water bath of 37° C. for 3050 minutes. Preferably, the collagen used in the present application may have a mass concentration of 50% (m/v) and a relative molecular weight ranging from 1600 to 4000, and collagen I is used here preferably.

At last, in step 6, the phosphate buffer is added for cell washing and re-suspending. Specifically, the phosphate buffer of 30 ml is slowly added into and mixed within the centrifuge tube C, and the phosphate buffer is being added while the centrifuge tube is being rotated. After adding, the cover of the centrifuge tube is covered, and the centrifuge tube C is rotated to achieve full washing. The centrifuge tube C is centrifuged for 10 minutes at 1500 rpm at room temperature, the supernatant is removed, and the 1640 complete culture medium is added into the centrifuge tube C to re-suspend the cells and to obtain fusion cells.

The preparation process of the phosphate buffer of the present application comprises the following steps: dissolving 8 g NaCl, 0.2 g KCl, 1.44 g $Na_2HPO_4 \cdot 2H_2O$ and 0.24 g $KH_2PO_4$ and adding distilled water to 1 L to prepare 0.01M PBS, adjusting pH to 7.2-7.4 and performing autoclaved sterilization.

The 1640 complete culture medium of the present application can be prepared following some steps listed below.

In step 1), the culture medium is dissolved, where one third of water is used to dissolve dehydrated medium and an inner surface of a packaging bag containing the dehydrated medium is washed twice by the remaining water. The water used for washing the packaging bag is then poured into culture solution, and the dissolving is improved by vibration.

In step 2), antibiotics can be added into the culture medium, where penicillin with a final concentration of 100 U/ml and streptomycin with a final concentration of 100 U/ml are achieved here. After that, some water is added to the culture medium to 900 ml (in the case that the addition of 10% calf serum is needed) and then pH is adjusted to 7.2 with 5% $NaHCO_3$.

In step 3), the culture medium is filtrated to remove bacteria. A filter membrane of 0.45 μm on top and another filter membrane of 0.22 μm below are used for filtration. The filtrated culture medium is separately loaded into bottles of 200 ml.

In step 4), 10% calf serum is added.

Figure 2A:
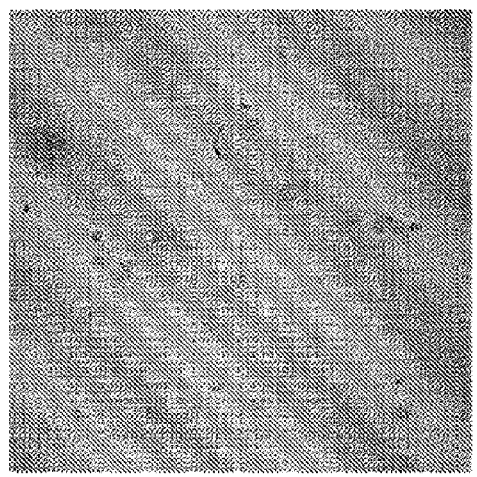
FIGS. 2a-2e are all photos of fusion cells obtained without using collagen under a confocal microscope.
Figure 2B:
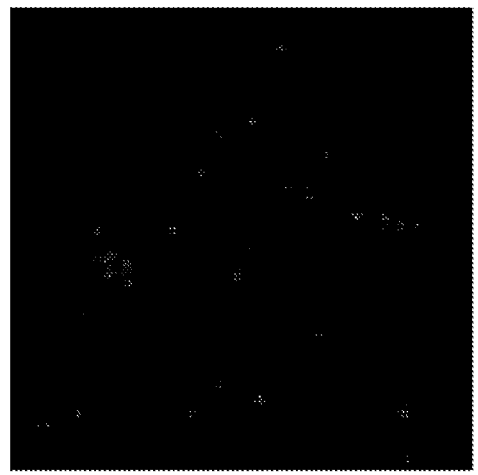
Figure 2C:
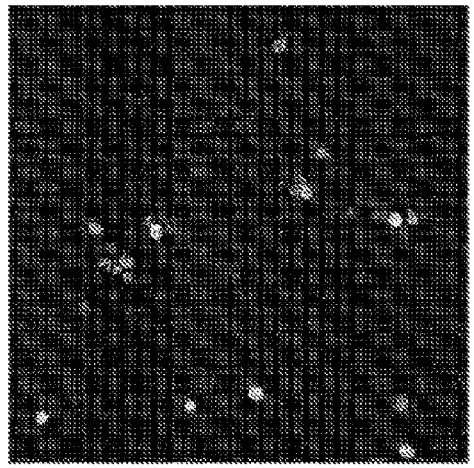
Figure 2D:
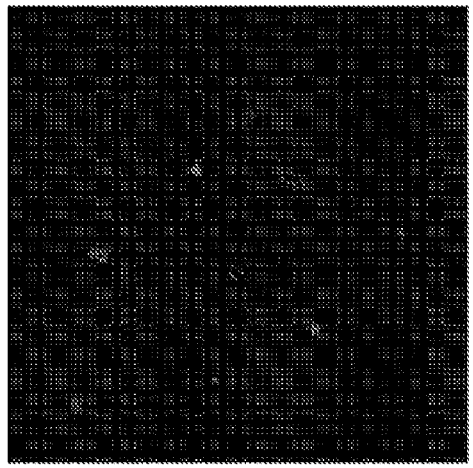
Figure 2E:
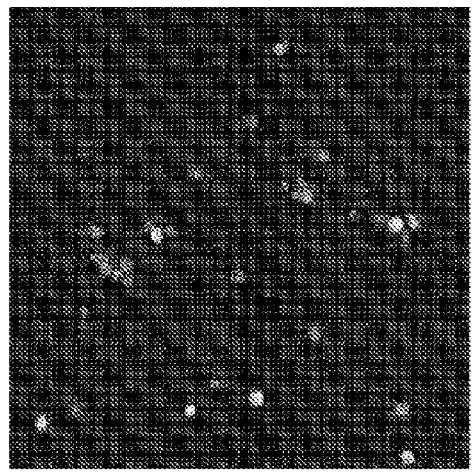

FIGS. 2a-2e are all photos of fusion cells obtained without using the collagen under a confocal microscope. In the operating steps of the present application, the fusion cells obtained without using the collagen can be got without performing the step 5, where mouse dendritic cells and mouse melanoma cells are respectively used as the dendritic cells and the tumour cells. Specifically, FIG. 2a is a photo of fusion cells obtained without using the collagen under the confocal microscope with a bright field of 20×; FIG. 2b is a photo of fusion cells obtained without using the collagen under the confocal microscope of 20×, where cell nucleus of the fusion cells in FIG. 2b are stained by DAPI; FIG. 2c is a photo of the murine dendritic cells stained with CSFE without using the collagen under the confocal microscope of 20×; FIG. 2d is a photo of the mouse melanoma cells stained with PKH26 without using the collagen under the confocal microscope of 20×; FIG. 2e is a photo by combining FIG. 2c with FIG. 2d.

Figure 3A:
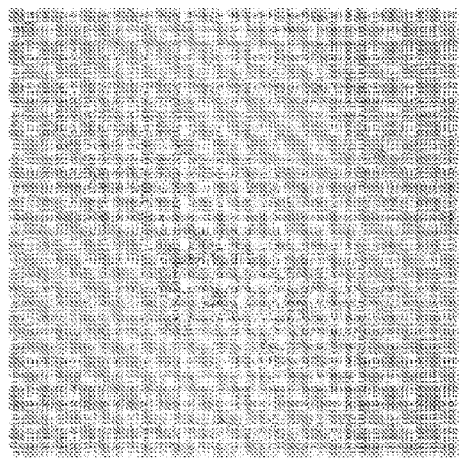
FIGS. 3a-3e are all photos of fusion cells obtained using collagen under a confocal microscope.
Figure 3B:
Figure 3C:
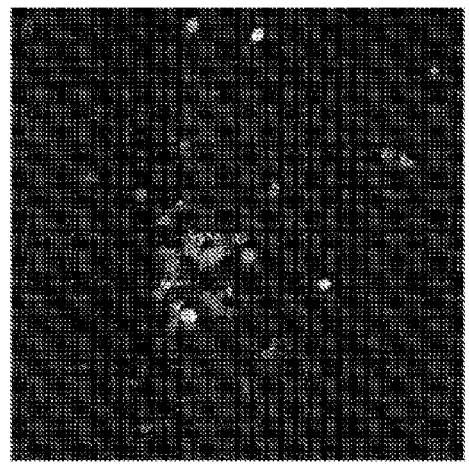
Figure 3D:
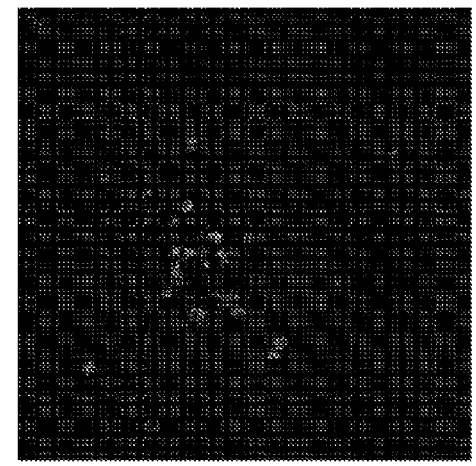
Figure 3E:
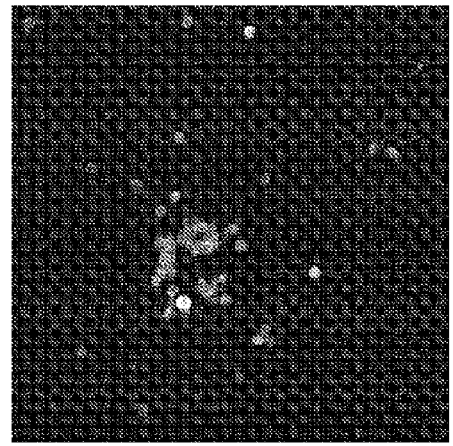

FIGS. 3a-3e are all photos of fusion cells obtained using the collagen under the confocal microscope, where samples of these photos are obtained by the method for cell fusion of the present application aforementioned, and materials and parameters used in each step are the same as those when preparing samples in FIGS. 2a-2e. Mouse dendritic cells and mouse melanoma cells are also respectively used as the dendritic cells and the tumour cells, while the only difference is that no collagen is added into the samples in FIGS. 2a-2e. Specifically, FIG. 3a is a photo of fusion cells obtained using the collagen under the confocal microscope with a bright field of 20×; FIG. 3b is a photo of fusion cells obtained using the collagen under the confocal microscope of 20×, where cell nucleus of the fusion cells in FIG. 3b are stained by DAPI; FIG. 3c is a photo of the mouse dendritic cells stained with CSFE in case of using the collagen under the confocal microscope of 20×; FIG. 3d is a photo of the mouse melanoma cells stained with PKH26 in case of using the collagen under the confocal microscope of 20×; FIG. 3e is a photo by combining FIG. 3c with FIG. 3d.

Figure 4:
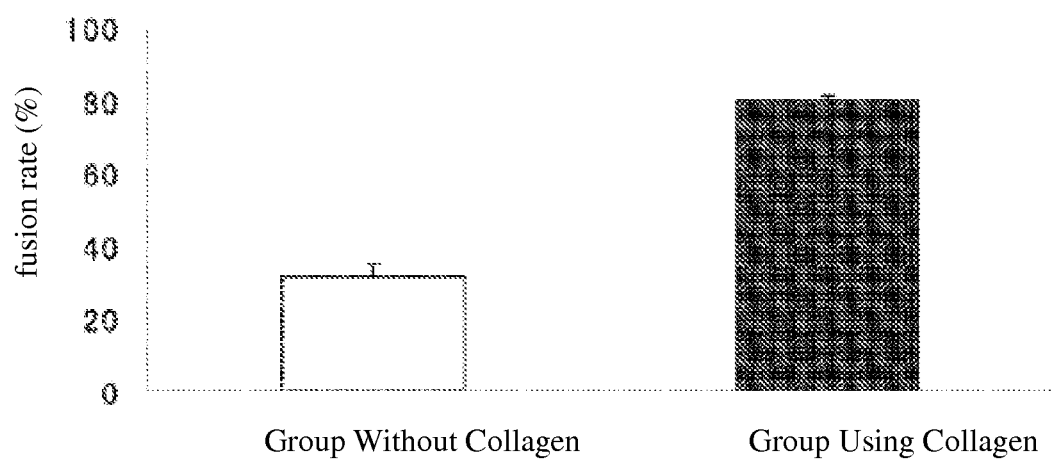
FIG. 4 is a comparison of fusion rate between cell fusion processes using and without using the collagen.

When compared FIGS. 2a-2e with FIGS. 3a-3e, it is obvious that an increased number of mouse dendritic cells and mouse melanoma cells are fused with each other when using the collage in FIGS. 3a-3e. FIG. 4 is the comparison of fusion rate between the cell fusion processes between using and without using the collagen . It can be seen from FIG. 4 that the fusion rate is as high as about 80% in case of using the collagen for cell fusion, while the fusion rate is about 30% without using the collagen for cell fusion. Thus the cell fusion rate can be efficiently improved by adding the collagen in the method for inducing fusion of dendritic cell with tumour cell of the present application.

The polyethylene glycol adopted in the present application can make the lipid molecules of the plasma membrane at the contact point between the two cells disperse and recombine, and then the cells fuse due to the mutual affinity between the bilayer membranes at the interface of the two cells and the surface tension between each other. The collagen can retrench and repair the cell membrane after fusion, thereby forming stable fusion cells. The method of the present application is proved to be high in fusion efficiency and low in cell damage by detections of fluorescence microscope and confocal microscope and cell experiments.

Embodiment 1

Mouse dendritic cells and B16 mouse melanoma cells are selected to be fused, and the fusion process comprises the following steps.

(1) First, the phosphate buffer, the collagen and the 1640 complete culture medium are respectively placed in the water bath of 37° C. for latter usage.

(2) The B16 mouse melanoma cells are digested and collected into the centrifuge tube A of 50 ml, the mouse dendritic cells are collected into the centrifuge tube B of 50 ml, and the centrifuge tube A and the centrifuge tube B are respectively centrifuged for 10 minutes at 1500 rpm at room temperature.

(3) The phosphate buffer of 20 ml is added into the centrifuge tube A and the centrifuge tube B respectively to re-suspend the cells, and cell counting is performed thereafter in these two centrifuge tubes.

(4) The two types of cells respectively in the centrifuge tube A and in the centrifuge tube B are both added into the centrifuge tube C of 50 ml according to a quantity proportion of the B16 mouse melanoma cells to the mouse dendritic cells of 1 to 2. The total number of the cells is controlled to range from $1 \times 10^7$ to $5 \times 10^7$, and the cells are mixed by whirling.

(5) The centrifuge tube C is centrifuged for 10 minutes at 1500 rpm at room temperature.

(6) Supernatant is removed, and the centrifuge tube C is flicked with fingers to achieve relatively uniform cell distribution. Then the centrifuge tube C is placed into the water bath of 40° C. for 3 minutes.

(7) The polyethylene glycol with a molecular weight of 1500 and a mass concentration of 50% (m/v) is placed in the water bath of 40° C. for 2 minutes.

(8) The polyethylene glycol of 200 μl heated by the water bath is added into the centrifuge tube C using a pipette within one minute, where the pipette tip is being rotated during the adding process and the cells are stirred by the pipette tip after finishing the addition of PEG. The centrifuge tube C is then placed in the water bath of 40° C. for 3-5 minutes.

(9) The phosphate buffer of 1 ml is added into the centrifuge tube C to stop reacting, and this adding operation is required to be finished within one minute. Then the phosphate buffer of 30 ml-40 ml is slowly added into the centrifuge tube C together with rotating the centrifuge tube C. After adding, the cover of the centrifuge tube is covered, and the centrifuge tube is rotated to mix the solution to achieve full reaction termination.

(10) The centrifuge tube C is centrifuged for 10 minutes at 1500 rpm at room temperature.

(11) The supernatant is removed, and the phosphate buffer of 30 ml-40 ml is slowly added into and mixed within the centrifuge tube C (e.g., within 3-5 minutes), and the centrifuge tube C is being rotated during the adding process. After adding, the cover of the centrifuge tube is covered, and the centrifuge tube is rotated to achieve full washing.

(12) The centrifuge tube C is again centrifuged for 10 minutes at 1500 rpm at room temperature.

(13) The supernatant is removed, and the phosphate buffer of 350 µl is added into the centrifuge tube C to re-suspend the cells.

(14) The collagen of 3 µl-5 µl is added into the centrifuge tube C and the centrifuge tube C is placed in the water bath of 37° C. for 30-50 minutes. The collagen used here can have a relative molecular weight of 1600 and a mass concentration of 50% (m/v).

(15) The phosphate buffer of 30 ml is slowly added into and mixed within the centrifuge tube C, and the phosphate buffer is being added while the centrifuge tube is being rotated. After adding, the cover of the centrifuge tube is covered, and the centrifuge tube is rotated to achieve full washing.

(16) The centrifuge tube C is centrifuged for 10 minutes at 1500 rpm at room temperature.

(17) The supernatant is removed, and the 1640 complete culture medium is added into the centrifuge tube C to re-suspend the cells and to obtain the fusion cells thereafter.

The fusion cells obtained by this embodiment are high in efficiency and suitable for murine tumour vaccine research.

Embodiment 2

Human dendritic cells and A549 human lung cancer cells are selected to be efficiently fused, and the fusion process comprises the following steps.

(1) First, the phosphate buffer, the collagen and the 1640 complete culture medium are respectively placed in the water bath of 37° C. for latter usage.

(2) The A549 human lung cancer cells are digested and collected into the centrifuge tube A of 50 ml, the human dendritic cells are collected into the centrifuge tube B of 50 ml, and the centrifuge tube A and the centrifuge tube B are respectively centrifuged for 10 minutes at 1500 rpm at room temperature.

(3) The phosphate buffer of 10-20 ml is added into the centrifuge tube A and the centrifuge tube B respectively to re-suspend the cells for cell counting.

(4) The two types of cells respectively in the centrifuge tube A and in the centrifuge tube B are both added into the centrifuge tube C of 50 ml according to a quantity proportion of the A549 human lung cancer cells to the human dendritic cells of 1 to 5. The total number of the cells is controlled to range from $1 \times 10^7$ to $5 \times 10^7$, and the cells are mixed by whirling.

(5) The centrifuge tube C is centrifuged for 10 minutes at 1500 rpm at room temperature.

(6) Supernatant is removed, and the centrifuge tube C is flicked with fingers to achieve relatively uniform cell distribution. Then the centrifuge tube C is placed into the water bath of 40° C. for 5 minutes.

(7) The polyethylene glycol with a molecular weight of 3000 and with a mass concentration of 50% (m/v) is placed in the water bath of 40° C. for 2 minutes.

(8) The polyethylene glycol of 1000 µl heated by the water bath is added into the centrifuge tube C using a pipette within one minute, where the pipette tip is being rotated during the adding process and the cells are stirred by the pipette tip after finishing the addition of PEG. The centrifuge tube C is placed in the water bath of 40° C. for 5 minutes.

(9) The phosphate buffer of 1 ml is added into the centrifuge tube C to stop reacting, and this adding operation is required to be finished within one minute. Then the phosphate buffer of 30 ml is slowly added into the centrifuge tube C together with the rotation of the centrifuge tube C. After adding, the cover of the centrifuge tube is covered, and the centrifuge tube is rotated to mix the solution to achieve full reaction termination.

(10) The centrifuge tube C is centrifuged for 10 minutes at 1500 rpm at room temperature.

(11) The supernatant is removed, and the phosphate buffer of 40 ml is slowly added into and mixed within the centrifuge tube C (e.g., within 3-5 minutes), and the centrifuge tube C is being rotated during the adding process. After adding, the cover of the centrifuge tube is covered, and the centrifuge tube is rotated to achieve full washing.

(12) The centrifuge tube C is again centrifuged for 10 minutes at 1500 rpm at room temperature.

(13) The supernatant is removed, and the phosphate buffer of 200 µl is added into the centrifuge tube C to re-suspend the cells.

(14) The collagen of 2 µl-8 µl is added into the centrifuge tube C, which is then placed in the water bath of 37° C. for 30-50 minutes. The collagen adopted here can have a relative molecular weight of 4000 and a mass concentration of 50% (m/v).

(15) The phosphate buffer of 30 ml is slowly added into and mixed within the centrifuge tube C, and the phosphate buffer is being added while the centrifuge tube is being rotated. After adding, the cover of the centrifuge tube is covered, and the centrifuge tube is rotated to achieve full washing.

(16) The centrifuge tube C is centrifuged for 10 minutes at 1500 rpm at room temperature.

(17) The supernatant is removed, and the 1640 complete culture medium is added into the centrifuge tube C to re-suspend the cells and to obtain the fusion cells thereafter.

The fusion cells obtained by this embodiment are high in efficiency and suitable for human tumour vaccine research.

Embodiment 3

DC2.4 cells and B16 mouse melanoma cells are selected for cell fusion, and the fusion process comprises the following steps.

(1) First, the phosphate buffer, the collagen and the 1640 complete culture medium are respectively placed in the water bath of 37° C. for latter usage.

(2) The B16 mouse melanoma cells are digested and collected into the centrifuge tube A of 50 ml, the DC2.4 cells are collected into the centrifuge tube B of 50 ml, and the centrifuge tube A and the centrifuge tube B are respectively centrifuged for 10 minutes at 1500 rpm at room temperature.

(3) The phosphate buffer of 10-20 ml is added into the centrifuge tube A and the centrifuge tube B respectively to re-suspend the cells for cell counting.

(4) The two types of cells respectively in the centrifuge tube A and in the centrifuge tube B are both added into the centrifuge tube C of 50 ml according to a quantity proportion of the B16 mouse melanoma cells to the DC2.4 cells of 1 to 2. The total number of the cells is controlled to range from $1 \times 10^7$ to $5 \times 10^7$, and the cells are mixed by whirling.

(5) The centrifuge tube C is centrifuged for 10 minutes at 1500 rpm at room temperature.

(6) Supernatant is removed, and the centrifuge tube C is flicked with fingers to achieve relative uniform cell distribution. Then the centrifuge tube C is placed into the water bath of 40° C. for 3 minutes.

(7) The polyethylene glycol with a molecular weight of 6000 and a mass concentration of 50% (m/v) is placed in the water bath of 40° C. for 2 minutes.

(8) The polyethylene glycol of 600 µl heated by the water bath is added into the centrifuge tube C using a pipette within one minute, where the pipette tip is being rotated during the adding process and the cells are stirred by the pipette tip after finishing the addition of PEG. The centrifuge tube C is placed in the water bath of 40° C. for 3 minutes.

(9) The phosphate buffer of 1 ml is added into the centrifuge tube C to stop reacting, and this addition operation is required to be finished within one minute. Then the phosphate buffer of 40 ml is slowly added into the centrifuge tube C, and the phosphate buffer is being added while the centrifuge tube C is being rotated. After adding, the cover of the centrifuge tube is covered, and the centrifuge tube is rotated to mix the solution to achieve full reaction termination.

(10) The centrifuge tube C is centrifuged for 10 minutes at 1500 rpm at room temperature.

(11) The supernatant is removed, and the phosphate buffer of 30 ml is slowly added into and mixed within the centrifuge tube C (e.g., within 3-5 minutes), and the phosphate buffer is being added while the centrifuge tube C is being rotated. After adding, the cover of the centrifuge tube is covered, and the centrifuge tube is rotated to achieve full washing.

(12) The centrifuge tube C is again centrifuged for 10 minutes at 1500 rpm at room temperature.

(13) The supernatant is removed, and the phosphate buffer of 800 µl is added into the centrifuge tube C to re-suspend the cells.

(14) The collagen of 2 µl-8 µl is added into the centrifuge tube C and placed in the water bath of 37° C. for 30-50 minutes. The collagen adopted here can have a relative molecular weight of 2000 and a mass concentration of 50% (m/v).

(15) The phosphate buffer of 30 ml is slowly added into and mixed within the centrifuge tube C, where the centrifuge tube is being rotated during the adding process. After adding, the cover of the centrifuge tube is covered, and the centrifuge tube is rotated to achieve full washing.

(16) The centrifuge tube C is centrifuged for 10 minutes at 1500 rpm at room temperature.

(17) The supernatant is removed, and the 1640 complete culture medium is added into the centrifuge tube C to re-suspend the cells and to obtain the fusion cells thereafter.

The fusion cells obtained by this embodiment are high in efficiency and suitable for hybrid cell research.

What is claimed is:

1. A method for inducing fusion of dendritic cell with tumour cell, wherein comprising the following steps:
   S1, collecting tumour cells in a centrifuge tube A, collecting dendritic cells in a centrifuge tube B, respectively centrifuging the centrifuge tube A and the centrifuge tube B for 10 minutes at 1500 rpm at room temperature, and counting the cells in the centrifuge tube A and the centrifuge tube B respectively after re-suspending the cells therein with phosphate buffer;
   S2, adding the tumour cells in the centrifuge tube A and the dendritic cells in the centrifuge tube B into a centrifuge tube C according to a quantity proportion of the tumour cells to the dendritic cells of 1 to 2-5 while controlling a total number of the cells to range from $1 \times 10^7$ to $5 \times 10^7$, mixing the cells by whirling, centrifuging the centrifuge tube C for 10 minutes at 1500 rpm at room temperature, removing the supernatant, and placing the centrifuge tube C in a water bath of 40° C. for 3-5 minutes;
   S3, placing polyethylene glycol with a molecular weight from 1500 to 6000 into the water bath of 40° C. for 2 minutes, adding 200 µl-1000 µl of the polyethylene glycol into the centrifuge tube C within one minute, mixing the cells, and placing the centrifuge tube C in the water bath of 40° C. for 3-5 minutes;
   S4, first adding 1ml of phosphate buffer into the centrifuge tube C within one minute to stop reacting, then adding and mixing 30 ml-40 ml of the phosphate buffer in the centrifuge tube C within 3-5 minutes; centrifuging the centrifuge tube C for 10 minutes at 1500 rpm at room temperature, removing the supernatant, adding and mixing 30 ml-40 ml of the phosphate buffer in the centrifuge tube C; centrifuging the centrifuge tube C for 10 minutes at 1500 rpm at room temperature, removing the supernatant, and adding 200 µl-800 µl of the phosphate buffer into the centrifuge tube C to re-suspend the cells;
   S5, adding 2 µl-8 µl of collagen into the centrifuge tube C, and placing the centrifuge tube C in a water bath of 37° C. for 30-50 minutes;
   S6, adding and mixing 30 ml of the phosphate buffer in the centrifuge tube C, centrifuging the centrifuge tube C for 10 minutes at 1500 rpm at room temperature, removing the supernatant, adding 1640 complete culture medium into the centrifuge tube C and re-suspending the cells to obtain fusion cells.

2. The method for inducing fusion of dendritic cell with tumour cell of claim 1, wherein, the collagen of the step S5 has a relative molecular weight ranging from 1600 to 4000 and a mass-to-volume ratio of 50%.

3. The method for inducing fusion of dendritic cell with tumour cell of claim 1, wherein, the collagen of the step S5 is collagen I.

4. The method for inducing fusion of dendritic cell with tumour cell of claim 1, wherein, the polyethylene glycol of the step S3 has a relative molecular weight ranging from 1600 to 4000 and a mass-to-volume ratio of 50%.

5. The method for inducing fusion of dendritic cell with tumour cell of claim 1, wherein, 300 µl-1000 of the polyethylene glycol is adopted in the step S3.

6. The method for inducing fusion of dendritic cell with tumour cell of claim 1, wherein the 1640 complete culture medium of the step S6 is prepared as follows:
   dissolving dehydrated medium by water to obtain a culture medium;
   adding antibiotics into the culture medium, wherein the antibiotics comprises penicillin with a final concentration of 100 U/ml and streptomycin with a final concentration of 100 U/ml;
   adding extra water into the culture medium containing the antibiotics and adjusting its pH to 7.2 with 5% $NaHCO_3$;
   filtering the culture medium containing the antibiotics by a filter membrane of 0.45 µm on top and another filter membrane of 0.22 µm below; and
   adding 10% calf serum into the filtered culture medium to obtain the 1640 complete culture medium.

* * * * *

UNITED STATES PATENT AND TRADEMARK OFFICE
CERTIFICATE OF CORRECTION

PATENT NO. : 9,499,798 B2  
APPLICATION NO. : 14/426163  
DATED : November 22, 2016  
INVENTOR(S) : Lu et al.

Page 1 of 1

It is certified that error appears in the above-identified patent and that said Letters Patent is hereby corrected as shown below:

On the Title Page

At Item (72), Inventors:  
At Line 2 after (CN) add, Yongxiang Zhao, Nanning (CN)

Signed and Sealed this
Seventeenth Day of March, 2020

Andrei Iancu
*Director of the United States Patent and Trademark Office*

UNITED STATES PATENT AND TRADEMARK OFFICE
CERTIFICATE OF CORRECTION

PATENT NO. : 9,499,798 B2  
APPLICATION NO. : 14/426163  
DATED : November 22, 2016  
INVENTOR(S) : Yongxiang Zhao et al.

Page 1 of 1

It is certified that error appears in the above-identified patent and that said Letters Patent is hereby corrected as shown below:

On the Title Page

Item (12) "Lu et al." should read -- Zhao et al. --.

Signed and Sealed this  
Twenty-sixth Day of May, 2020

Andrei Iancu  
*Director of the United States Patent and Trademark Office*